US009498420B2

(12) United States Patent
Laughlin, II et al.

(10) Patent No.: US 9,498,420 B2
(45) Date of Patent: Nov. 22, 2016

(54) COSMETIC COMPOSITIONS AND METHODS FOR INHIBITING MELANIN SYNTHESIS

(71) Applicant: The Procter & Gamble Company, Cincinnati, OH (US)

(72) Inventors: Leo Timothy Laughlin, II, Mason, OH (US); Tomohiro Hakozaki, Cincinnati, OH (US); Shuhei Tanaka, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 241 days.

(21) Appl. No.: 14/267,512

(22) Filed: May 1, 2014

(65) Prior Publication Data

US 2014/0328775 A1    Nov. 6, 2014

Related U.S. Application Data

(60) Provisional application No. 61/817,961, filed on May 1, 2013.

(51) Int. Cl.

| | | |
|---|---|---|
| *A61Q 17/04* | (2006.01) | |
| *A61Q 19/02* | (2006.01) | |
| *A61K 8/42* | (2006.01) | |
| *A61K 8/34* | (2006.01) | |
| *A61K 8/368* | (2006.01) | |
| *A61K 8/49* | (2006.01) | |
| *A61K 8/60* | (2006.01) | |
| *A61K 8/67* | (2006.01) | |
| *A61K 8/97* | (2006.01) | |
| *A61K 8/44* | (2006.01) | |
| *A61K 36/03* | (2006.01) | |
| *A61K 36/484* | (2006.01) | |
| *A61K 36/60* | (2006.01) | |

(52) U.S. Cl.
CPC . *A61K 8/42* (2013.01); *A61K 8/34* (2013.01); *A61K 8/342* (2013.01); *A61K 8/345* (2013.01); *A61K 8/368* (2013.01); *A61K 8/44* (2013.01); *A61K 8/498* (2013.01); *A61K 8/60* (2013.01); *A61K 8/675* (2013.01); *A61K 8/678* (2013.01); *A61K 8/97* (2013.01); *A61K 36/03* (2013.01); *A61K 36/484* (2013.01); *A61K 36/60* (2013.01); *A61Q 17/04* (2013.01); *A61Q 19/02* (2013.01)

(58) Field of Classification Search
None
See application file for complete search history.

(56) References Cited

U.S. PATENT DOCUMENTS

| | | | |
|---|---|---|---|
| 5,621,012 A | 4/1997 | Schonrock et al. | |
| 8,524,204 B2 | 9/2013 | Hakozaki et al. | |
| 2002/0106384 A1 | 8/2002 | Zhang et al. | |
| 2007/0264362 A1 | 11/2007 | Yoshpe et al. | |
| 2008/0169215 A1 | 7/2008 | Tanaka et al. | |
| 2009/0148391 A1 | 6/2009 | Schmaus et al. | |
| 2009/0238905 A1 | 9/2009 | Gurney et al. | |
| 2010/0015071 A1* | 1/2010 | Park | A23L 1/3002 424/59 |
| 2011/0081433 A1 | 4/2011 | Kaur et al. | |
| 2011/0097286 A1 | 4/2011 | Swanson et al. | |
| 2011/0110874 A1 | 5/2011 | Tanaka et al. | |
| 2012/0128603 A1 | 5/2012 | Tanaka | |
| 2012/0148510 A1 | 6/2012 | Hakozaki et al. | |
| 2012/0156146 A1 | 6/2012 | Hakozaki et al. | |

FOREIGN PATENT DOCUMENTS

| | | |
|---|---|---|
| CN | 101578086 A | 11/2009 |
| CN | 102198055 B | 11/2012 |
| DE | 44 20 625 C1 | 11/1995 |
| DE | 195 38 555 A1 | 4/1997 |
| EP | 0 687 467 A2 | 12/1995 |
| EP | 0 769 291 B1 | 3/2003 |
| EP | 2 522 331 A1 | 11/2012 |
| ES | 2 193 218 T3 | 11/2003 |
| GB | 2 422 107 B | 12/2008 |
| JP | 8003034 A | 1/1996 |
| JP | 2009-522337 A | 6/2009 |
| JP | 2010-515720 A | 5/2010 |
| KR | 2009-0089459 A | 8/2009 |
| WO | 2007/077259 A9 | 7/2007 |
| WO | 2008/087591 A1 | 7/2008 |

OTHER PUBLICATIONS

G. O. Leite et al., (−)-α-Bisabolol attenuates visceral nociception and inflammation in mice, Fitoterapia 82 (2011), pp. 208-211.
N. F. M. Rocha et al., Anti-nociceptive and anti-inflammatory activities of (−)-α-bisabolol in rodents, Naunyn-Schmiedeberg's Arch Pharmacol (2011) 384: pp. 525-533.
J. M. Gillbro et al., The melanogenesis and mechanisms of skin-lightening agents—existing and new approaches, International Journal of Cosmetic Science, 2011, 33, pp. 210-221.
Philosophy Miracle Worker Dark Spot Corrector, http://www.gnpd.com, May 2012 (5 pages).
Trimalla Bhatta, Yogatrangini—Commentary by Duttarama Mathura:, 05(p. 04-08), ( Ref.p. of publication:263 ), Edn. Reprint 2003, Chaukhamba Vidyabhavan, Varanasi, India.†
Acharya Gulraj Sharma Mishra, Siddaprayogalatika-, 05 (p. 09-13), ( Ref.p. of publication:220 ), Ed. 2nd 2005, Translated by Vd.Shivakaran Sharma Chhangani, Varanasi, India.†
Mohammad Akmal Khan, Qaraabaadeen Azam wa Akmal (20th century AD), 04 (p. 14-17), ( Ref.p. of publication:347 ), 1897 AD, Delhi / Matba Mustafai, India.†

\* cited by examiner
† cited by third party

*Primary Examiner* — Nannette Holloman
(74) *Attorney, Agent, or Firm* — Betty J. Zea

(57) ABSTRACT

A cosmetic composition suitable for topical application, for example, is provided. In some examples, the cosmetic composition may include batyl alcohol, undecylenoyl phenylalanine, hexyldecanol, and bisabolol. A method of reducing the synthesis of melanin by using the cosmetic compositions is also disclosed herein.

20 Claims, No Drawings

COSMETIC COMPOSITIONS AND METHODS FOR INHIBITING MELANIN SYNTHESIS

TECHNICAL FIELD

The present disclosure generally relates to cosmetic compositions including batyl alcohol, bisabolol, hexyldecanol, and undecylenoyl phenylalanine; and methods relating thereto.

BACKGROUND

Consumers often desire skin lightening products that are affordable, safe, stable, and can produce consumer-noticeable skin lightening after routine use. In this regard, consumers may desire skin lightening products to either lighten the color of their skin and/or minimize skin spots or blotchiness. For example, consumers may desire skin lightening agents to counteract fluctuations in skin color brought about by hormonal fluctuations or environmental stressors like UV light.

At least some skin lightening agents work by targeting or influencing one or more of the steps involved in the development of skin color. Human skin color is attributed in part to the outermost layer of skin (i.e. epidermis) where many melanocytes may be located. The synthesis of melanin, pigments that may be dark brown/black or light red-yellow, is a complex process that involves the enzyme, tyrosinase, and can take place within the melanosomes of the melanocytes. These melanosomes may be transferred from the melanocyte to the keratinocytes.

While the effects of certain individual ingredients on skin pigment have been studied to some degree, the role that combinations of ingredients might play in the appearance of skin color appears to be less well studied, including how varying concentrations, ratios and/or combinations of ingredients might affect the pigment of the skin.

SUMMARY

A cosmetic composition suitable for topical application is provided. In some examples, the cosmetic composition comprises N-undecylenoyl-L-phenylalanine; hexyldecanol; bisabolol; and batyl alcohol.

A method for reducing melanin synthesis is also provided. In some examples, the method comprises: identifying a target portion of keratinous tissue in need of melanin reduction; and topically applying to the target portion of the keratinous tissue an effective amount of a cosmetic composition comprising: N-undecylenoyl-L-phenylalanine; hexyldecanol; bisabolol; and batyl alcohol.

DETAILED DESCRIPTION

All percentages are weight percentages based on the weight of the composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

"Cosmetic composition" means compositions suitable for topical application on mammalian keratinous tissue.

"Derivatives" include, but are not limited to, amide, ether, ester, amino, carboxyl, acetyl, and/or alcohol derivatives of a given chemical.

"Effective amount" means an amount sufficient to induce one or more biological effects. Non-limiting examples of biological effects include a change in skin color and/or a change in the synthesis of melanin (either in vitro or in vivo) such as a decrease in melanin synthesis.

"Extract" as used herein, means material that may be obtained by the following procedure: Place the indicated portion of dried plant material (stem, bark, leaves, etc.) in a conical glass percolator. Add the indicated percentage of extraction solvent in a w/w ratio of 1 part plant material to 2 parts extraction solvent. When the indicated percentage of extraction solvent is less than 100%, the remaining solvent is water (e.g., 95% ethanol with 5% water, 50% ethanol with 50% water, etc.). Allow the extraction to proceed for about 16 to about 24 hours. Collect the percolate, and repeat the above process until the resulting percolate is substantially free from plant additional extract. Combine the percolates, evaporate to dryness under reduced pressure, and store the resulting extract under nitrogen at less than 4 degrees Celsius.

"Hyperpigmentation" as used herein, refers to an area of skin wherein the pigmentation is greater than that of an adjacent area of skin (e.g., a pigment spot, an age spot, and the like).

"Improve skin condition" or "improving skin condition" means effecting a visually and/or tactilely perceptible positive change, or benefit, in skin appearance and feel. Benefits that may be provided include, but are not limited to, one or more of the following: reducing the appearance of wrinkles and coarse deep lines, fine lines, crevices, bumps, and large pores; thickening of keratinous tissue (e.g., building the epidermis and/or dermis and/or sub-dermal layers of the skin, and where applicable the keratinous layers of the nail and hair shaft, to reduce skin, hair, or nail atrophy); increasing the convolution of the dermal-epidermal border (also known as the rete ridges); skin lightening; preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, under-eye circles, blotchiness (e.g., uneven red coloration due to, for example, rosacea), sallowness, discoloration caused by hyperpigmentation, etc.

"Keratinous tissue" refers to keratin-containing layers disposed as the outermost protective covering of mammals which include, but are not limited to, skin, hair, nails, and cuticles.

"Sallowness" means the pale color, yellow color or the like condition of skin that occurs as a result of a loss of, damage to, alterations to, and/or abnormalities in skin components such that they become colored (e.g., yellow in color) due to processes such as protein glycation and accumulation of lipofuscin or in the decrease in peripheral blood flow that typically accompanies skin aging.

"Salts" as used herein, include, but are not limited to sodium, potassium, calcium, ammonium, manganese, copper, and/or magnesium salts of a given chemical.

"Signs of skin aging" as used herein, include but are not limited to, all outward visibly and tactilely perceptible manifestations, as well as any macro- or microeffects, due to keratinous tissue aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

"Skin care actives" means chemicals that when applied to the skin, provide a benefit or improvement to the skin. It is to be understood that skin care actives are useful not only for application to skin, but also to hair, nails and other keratinous tissue.

Surprisingly, it has been discovered that a combination of batyl alcohol, bisabolol, undecylenoyl phenylalanine, and hexyldecanol may act synergistically to inhibit melanin synthesis. It has also been discovered that the synergistic combination of batyl alcohol, bisabolol, undecylenoyl phenylalanine, and hexyldecanol may include other known skin care actives such as niacinamide and still provide a synergistic effect. Without being limited to theory, it is believed that novel cosmetic compositions comprising batyl alcohol, bisabolol, undecylenoyl phenylalanine, and hexyldecanol may reduce melanin synthesis when topically applied to keratinous tissue. Such cosmetic compositions may be used, for example, to treat skin color irregularities (e.g. hyperpigmentation), lighten the color of the skin, ameliorate the signs of aging, and/or improve skin condition.

Surprisingly, it has been also been discovered that a combination of bisabolol, undecylenoyl phenylalanine, and hexyldecanol may act synergistically to inhibit melanin synthesis. Without being limited to theory, it is believed that this inhibition of melanin synthesis may lead to reduced melanin levels in the upper layers of the epidermis.

Table 1 below illustrates the effect of various test conditions on melanin synthesis using the Melanin Synthesis Assay disclosed herein. Sample 1 included 0.1% bisabolol (shown as "Bis"). Sample 2 included 0.1% bisabolol, 0.00056% hexyldecanol (shown as "HD"), and 0.00056% niacinamide (shown as "Nia"). Sample 3 included 0.1% bisabolol, 0.00011% undecylenoyl phenylalanine (shown as "UP"), and 0.00056% niacinamide. Sample 4 included 0.00056% hexyldecanol, 0.00011% undecylenoyl phenylalanine, and 0.00056% niacinamide. Sample 5 included 0.1% bisabolol, 0.00056% hexyldecanol, and 0.00011% undecylenoyl phenylalanine. Sample 6 included 0.1% bisabolol, 0.00056% hexyldecanol, 0.00011% undecylenoyl phenylalanine, and 0.00056% niacinamide.

TABLE 1

| Sample | Test Conditions | Average Melanin % Inhibition | P-Value versus HD/UP/Nia |
|---|---|---|---|
| 1 | Bis | 2.2 | 0.9795 |
| 2 | Bis/HD/Nia | 3.2 | 0.9883 |
| 3 | Bis/UP/Nia | −2.8 | 0.9914 |
| 4 | HD/UP/Nia | 4.5 | — |
| 5 | Bis/HD/UP | 60.9 | 0.0269 |
| 6 | Bis/HD/UP/Nia | 48.5 | 0.0134 |

Comparing Sample 1 to Sample 4, bisabolol alone did not significantly reduce the production of melanin from B16-F1 mouse melanoma cells as compared to Sample 4 which included a combination of hexyldecanol, undecylenoyl phenylalanine, and niacinamide. Comparing Sample 2 to Sample 4, the combination of bisabolol, hexyldecanol, and niacinamide did not significantly reduce the production of melanin from B16-F1 mouse melanoma cells as compared to sample 4. Comparing Sample 3 to Sample 4, the combination of bisabolol, undecylenoyl phenylalanine, and niacinamide did not significantly reduce the production of melanin from B16-F1 mouse melanoma cells as compared to sample 4.

Unexpectedly, when bisabolol was combined with undecylenoyl phenylalanine and hexyldecanol as in Sample 5, a significant reduction was observed in the production of melanin from B16-F1 mouse melanoma cells as compared to Sample 4 which included a combination of hexyldecanol, undecylenoyl phenylalanine, and niacinamide. Comparing Sample 6 to Sample 4, the addition of niacinamide to a combination of bisabolol, undecylenoyl phenylalanine, and hexyldecanol as in Sample 6 resulted in a significant reduction in the production of melanin from B16-F1 mouse melanoma cells as compared to Sample 4 which included a combination of hexyldecanol, undecylenoyl phenylalanine, and niacinamide. These unexpected results suggest that cosmetic compositions including bisabolol, undecylenoyl phenylalanine, and hexyldecanol may be able to reduce the production of melanin when topically applied to keratinous tissue. These results also suggest that a synergistic combination of bisabolol, undecylenoyl phenylalanine, and hexyldecanol may include niacinamide and still provide a synergistic effect.

Table 2 below illustrates the affect of various other test conditions on melanin synthesis using the Melanin Synthesis Assay disclosed herein. Sample 7 included the vector control, dimethyl sulfoxide. Sample 8 included 0.03% batyl alcohol (shown as "Bat"). Sample 9 included 0.0005% hexyldecanol, 0.0001% undecylenoyl phenylalanine, and 0.0005% niacinamide. Sample 10 included 0.03% batyl alcohol, 0.0005% hexyldecanol, 0.0001% undecylenoyl phenylalanine, and 0.0005% niacinamide. Sample 11 included 0.003% bisabolol, hexyldecanol, 0.0001% undecylenoyl phenylalanine, and 0.0005% niacinamide. Sample 12 included 0.03% batyl alcohol, 0.003% bisabolol, 0.0005% hexyldecanol, 0.0001% undecylenoyl phenylalanine, and 0.0005% niacinamide.

TABLE 2

| Sample | Test Conditions | Average Melanin % Inhibition | P-Value versus HD/UP/Nia | P-Value versus Bis/HD/UP/Nia |
|---|---|---|---|---|
| 7 | Control | 0 | 0.4769 | 0.0347 |
| 8 | Bat | 7 | 0.7362 | 0.0275 |
| 9 | HD/UP/Nia | 5 | — | 0.0080 |
| 10 | Bat/HD/UP/Nia | 5 | 0.9641 | 0.029313 |
| 11 | Bis/HD/UP/Nia | 17 | 0.0080 | — |
| 12 | Bat/Bis/HD/UP/Nia | 42 | 0.0001 | 0.0008 |

Comparing Sample 9 to Sample 7, no significant difference in the production of melanin from B16-F1 mouse melanoma cells was observed with a combination of hexyldecanol, undecylenoyl phenylalanine, and niacinamide as compared to a vector only control. Comparing Sample 8 to Sample 9, batyl alcohol alone did not significantly reduce the production of melanin from B16-F1 mouse melanoma cells as compared to Sample 9 which included a combination of hexyldecanol, undecylenoyl phenylalanine, and niacinamide. Comparing Sample 10 to Sample 9, the addition of batyl alcohol to a combination including hexyldecanol, undecylenoyl phenylalanine, and niacinamide did not significantly reduce the production of melanin from B16-F1 mouse melanoma cells as compared to Sample 9 which included hexyldecanol, undecylenoyl phenylalanine, and niacinamide.

Comparing Sample 11 to Sample 9, the combination of bisabolol, hexyldecanol, undecylenoyl phenylalanine, and niacinamide resulted in a significant reduction in melanin production from B16-41 mouse melanoma cells as compared to Sample 9 which did not include bisabolol. Comparing Sample 12 to Sample 9, the combination of batyl alcohol, bisabolol, hexyldecanol, undecylenoyl phenylalanine, and niacinamide resulted in a significant reduction in melanin production from B16-41 mouse melanoma cells as compared to Sample 9. Interestingly, the addition of batyl alcohol to a combination of bisabolol, hexyldecanol, undecylenoyl phenylalanine, and niacinamide resulted in a significant reduction in melanin production from B16-41 mouse melanoma cells (compare Sample 12 to Sample 11). These results suggest that cosmetic compositions including batyl alcohol, bisabolol, undecylenoyl phenylalanine, and hexyldecanol may be able to inhibit or reduce melanin synthesis. These data also suggest that batyl alcohol may be added to cosmetic compositions including niacinamide, bisabolol, undecylenoyl phenylalanine, and hexyldecanol to further reduce the production of melanin when topically applied to keratinous tissue.

Cosmetic Compositions

The cosmetic compositions may be applied to mammalian keratinous tissue, in particular to human skin. The cosmetic compositions may take various forms. For example, some non-limiting examples of forms include solutions, suspensions, lotions, creams, gels, toners, sticks, pencils, sprays, aerosols, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks, cosmetics (e.g. foundations, eye liners, eye shadows), and the like.

The cosmetic compositions may include batyl alcohol. In some examples, the cosmetic composition may comprise about 0.5% of batyl alcohol by weight of the cosmetic composition. In some examples, the cosmetic composition may comprise from about 0.03% to about 2% of batyl alcohol, by weight of the cosmetic composition. In some examples the cosmetic composition may comprise from about 0.03% to about 1% of batyl alcohol, by weight of the cosmetic composition. In some examples, the cosmetic composition may comprise from about 0.03% to about 2% of batyl alcohol, by weight of the cosmetic composition. In some examples, the cosmetic composition may comprise from about 0.03% to about 5% of batyl alcohol, by weight of the cosmetic composition.

Batyl alcohol may possess the following formula:

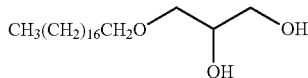

Cosmetic compositions may also include bisabolol. Bisabolol has previously been used as a fragrance ingredient in consumer products like fine fragrances, shampoos, soaps, and cosmetics. Bisabolol has also been implicated with possessing anti-inflammatory properties and has previously been included in compositions as an anti-inflammatory active.

Bisabolol may be naturally- or synthetically-derived, or may include a mixture of natural and synthetic origin. Bisabolol may be added to the cosmetic composition, for example, in pure form, as a salt, as an extract, or in any other form. Bisabolol includes, for example, "alpha-bisabolol," which includes (+)-alpha-bisabolol, (−)-alpha-bisabolol, (+)-epi-alpha-bisabolol, (−)-epi-alpha-bisabolol, and combinations thereof. The cosmetic compositions may include at least 0.003% of bisabolol, by weight of the cosmetic composition. The cosmetic compositions may include from about 0.003% to about 1%, from about 0.1% to about 1%, from about 0.003% to about 2%, from about 0.1% to about 2%, or from 0.003% to 5% of bisabolol, by weight of the cosmetic composition.

Bisabolol may possess the following formula:

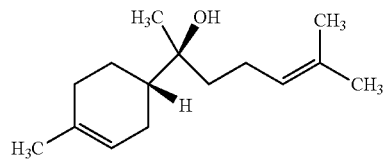 [SMILES: CC(C)=CCC[C@](C)(O)[C@@H]1CC=C(C)CC1]

Cosmetic compositions may also include N-undecylenoyl-L-phenylalanine (i.e. undecylenoyl phenylalanine). N-undecylenoyl-L-phenylalanine may be commercially available from SEPPIC and sold under the name of Sepiwhite®. N-undecylenoyl-L-phenylalanine is a material that belongs to a broad class of N-acyl phenylalanine derivatives and is known as a topical skin tone evening agent. The cosmetic compositions may include at least about 0.0001% or more of N-undecylenoyl-L-phenylalanine, by weight of the cosmetic composition. The cosmetic compositions may include from about 0.0001% to about 1%, from about 0.0001% to about 2%, from about 0.0001% to about 5%, or from about 0.01% to about 2% of N-undecylenoyl-L-phenylalanine, by weight of the cosmetic composition.

N-undecylenoyl-L-phenylalanine may possess the following formula:

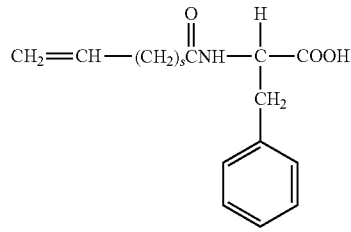

The cosmetic compositions may also include 2-hexyl-1-decanol (i.e. "hexyldecanol"). The cosmetic compositions described herein may have a concentration of hexyldecanol greater than 0.0005%, 0.1%, 0.5%, 1%, 2%, 3%, 4%, 5%, 6%, 8%, 10% or 12% and/or less than 20%, 18%, 16%, 15% or 14% by weight of the cosmetic composition. In some examples, the cosmetic compositions described herein may have a concentration of hexyldecanol of from about 0.01% to about 8%, from about 0.05% to about 5%, or from about 0.01% to about 8%, by weight of the cosmetic composition. Hexyldecanol may possess the following formula:

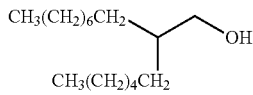

Cosmetic compositions may include vitamin B compounds. As used herein, vitamin B compounds include B1 compounds, B2 compounds, B3 compounds such as niacinamide, B5 compounds, such as panthenol or "pro-B5", pantothenic acid, pantothenyl, B6 compounds, such as pyroxidine, pyridoxal, pyridoxamine, carnitine, thiamine, and riboflavin. In some embodiments, the vitamin B compound is a B3 compound having the formula:

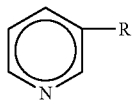

wherein R is —$CONH_2$ (i.e., niacinamide), —COOH (i.e., nicotinic acid) or —$CH_2OH$ (i.e., nicotinyl alcohol); derivatives thereof; and salts of any of the foregoing. In some examples, the cosmetic compositions may have a concentration of a vitamin B compound, by weight of the cosmetic composition, of greater than 0.0005%, 0.00056%, 1%, 2%, 3%, 4%, or 5% and/or less than 11%, 10%, 8%, or 6%. In some examples, the cosmetic compositions may have a concentration of a vitamin B compound, by weight of the cosmetic composition, of greater than about 0.0005%, 0.00056%, 1%, 2%, 3%, 4%, or 5% and/or less than about 11%, 10%, 8%, or 6%.

The topical application of niacinamide may be associated with a variety of cosmetic skin care benefits. These may include: i) normalization of age associated depletions of nicotinamide coenzymes in skin, ii) up-regulation of epidermal ceramide synthesis with concurrent epidermal barrier benefits, iii) protection against damage produced by UV irradiation, iv) inhibition of the transfer of melanosomes from melanocytes to keratinocytes (thereby providing a potential skin tone benefit), and reduction in sebaceous lipogenesis. Thus in certain instances, it may be desirable to include niacinamide in the cosmetic composition in order to improve the appearance of aging/photo-damaged skin.

The cosmetic compositions may also comprise one or more humectants. Some non-limiting examples of humectants include sorbitol, honey, propylene glycol, and glycerin. Glycerin, for example, is a small, polar molecule that is liquid at room temperature and miscible with water. Endogenous glycerin is believed to be an important component of skin hydration and topical application of cosmetic products containing glycerin can be associated with improvements in barrier function, induction of biomarkers associated with keratinocyte proliferation and wound healing, reduction in melanin intensity, increases in epidermal thickness, and improvements in general skin appearance. In some examples, the cosmetic compositions may include one or more humectants at a concentration, by weight of the cosmetic composition, of greater than 4%, 5%, 6%, 7%, 8%, 10%, 12%, 15%, 20% and/or less than 30%, 25%, or 20%. In some examples, the cosmetic compositions may include one or more humectants at a concentration, by weight of the cosmetic composition, of greater than about 4%, 5%, 6%, 7%, 8%, 10%, 12%, 15%, 20% and/or less than about 30%, 25%, or 20%.

The cosmetic compositions may also comprise hydroxycinnamic acid, inositol, licorice extract, glycyrrhetinic acid, glabridin, vitamin E succinate, salicylic acid, *Laminaria Saccharina* extract, *Ficus Bengalensis* extract, N-acetyl glucosamine, and combinations thereof.

Other Ingredients

In addition to the previously described ingredients, the cosmetic compositions described herein may also comprise one or more other ingredients. Non-limiting examples of other ingredients commonly used in cosmetic compositions (e.g., skin care actives), methods of identifying skin care actives and/or methods of formulating cosmetic compositions are described in U.S. Publications Nos. US2002/0022040; US2003/0049212; US2007/0196344; US2008/0181956; US2010/00092408; US2008/0206373; US 2010/0239510; US2010/0189669; US2011/0262025; US2011/0097286; US2012/0197016; US2012/0128683; US2012/0148515; US2012/0156146; and US2013/0022557 and U.S. Pat. Nos. 5,939,082; 5,872,112; 6,492,326; 6,696,049; 6,524,598; 5,972,359; and 6,174,533.

For example, the cosmetic composition may comprise from about 1% to about 95% by weight of water. The cosmetic composition may comprise from about 1% to about 95% by weight of one or more oils. The cosmetic composition may comprise from about 0.1%, 0.5%, 1%, 2%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, 5%, or 3% of the one or more oils. Oils may be used to solubilize, disperse, or carry materials that are not suitable for water or water soluble solvents. Suitable oils include silicones, hydrocarbons, esters, amides, ethers, and mixtures thereof. Oils may be fluid at room temperature. The oils may be volatile or nonvolatile. "Non-volatile" means a material that exhibits a vapor pressure of no more than about 0.2 mm of mercury at 25° C. at one atmosphere and/or a material that has a boiling point at one atmosphere of at least about 300° C. "Volatile" means that the material exhibits a vapor pressure of at least about 0.2 mm. of mercury at 20° C. Volatile oils may be used to provide a lighter feel when a heavy, greasy film is undesirable. When the cosmetic composition is in the form of an emulsion, oils are carriers typically associated with the oil phase. The cosmetic composition may be in the form of a water-in-oil emulsion, an oil-in-water emulsion, or a water-in-silicone emulsion.

Suitable oils include volatile oils. The volatile oils may have a viscosity ranging from about 0.5 to 5 centistokes at 25° C. Volatile oils may be used to promote more rapid drying of the cosmetic composition after it is applied to skin. Non-volatile oils are also suitable for use in the cosmetic composition. Non-volatile oils are often used for their emolliency and protective properties.

Suitable silicone oils include polysiloxanes. Polysiloxanes may have a viscosity of from about 0.5 to about 1,000,000 centistokes at 25° C. Such polysiloxanes can be represented by the general chemical formula:

$$R_3SiO[R_2SiO]_xSiR_3$$

wherein R is independently selected from hydrogen or $C_{1-30}$ straight or branched chain, saturated or unsaturated alkyl, phenyl or aryl, trialkylsiloxy; and x is an integer from 0 to about 10,000, chosen to achieve the desired molecular weight. Non-limiting examples of R include hydrogen, methyl, and ethyl. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500 100,000, and 300,000 centistokes.

Suitable dimethicones include those represented by the chemical formula:

$$R_3SiO[R_2SiO]_x[RR'SiO]_ySiR_3$$

wherein R and R' are each independently hydrogen or $C_{1-30}$ straight or branched chain, saturated or unsaturated alkyl, aryl, or trialkylsiloxy; and x and y are each integers of 1 to 1,000,000 selected to achieve the desired molecular weight. Non-limiting examples of dimethicones include phenyl dimethicone (Botansil™ PD-151 from Botanigenics, Inc.), diphenyl dimethicone (KF-53 and KF-54 from Shin-Etsu), phenyl trimethicone (556 Cosmetic Grade Fluid from Dow Corning), or trimethylsiloxyphenyl dimethicone (PDM-20, PDM-200, or PDM-1000 from Wacker-Belsil). Other non-limiting examples include alkyl dimethicones wherein at least R' is a fatty alkyl (e.g., $C_{12-22}$). A suitable alkyl dimethicone is cetyl dimethicone, wherein R' is a straight C16 chain and R is methyl. Cetyl dimethicone is available as 2502 Cosmetic Fluid from Dow Corning or as Abil Wax 9801 or 9814 from Evonik Goldschmidt GmbH.

Cyclic silicones are one type of silicone oil that may be used in the cosmetic composition. Such silicones have the general formula:

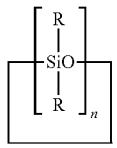

wherein R is independently selected from hydrogen or $C_{1-30}$ straight or branched chain, saturated or unsaturated alkyl, phenyl or aryl, trialkylsiloxy; and where n=3-8 and mixtures thereof. Commonly, a mixture of cyclomethicones is used where n is 4, 5, and/or 6. Commercially available cyclomethicones include Dow Corning UP-1001 Ultra Pure Fluid (i.e. n=4), Dow Corning XIAMETER® PMX-0245 (i.e. n=5), Dow Corning XIAMETER® PMX-0245 (i.e. n=6), Dow Corning 245 fluid (i.e. n=4 and 5), and Dow Corning 345 fluid (i.e. n=4, 5, and 6).

Suitable hydrocarbon oils include straight, branched, or cyclic alkanes and alkenes. The chain length may be selected based on desired functional characteristics such as volatility. Suitable volatile hydrocarbons may have between 6-20 carbon atoms or, alternately, between 8-16 carbon atoms.

Other suitable oils include esters. The suitable esters typically may contain at least 10 carbon atoms. These esters include esters with hydrocarbyl chains derived from fatty acids or alcohols (e.g., mono-esters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.). Exemplary esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, and oleyl adipate. Other suitable esters are further described in the Personal Care Product Council's *International Cosmetic Ingredient Dictionary and Handbook*, Thirteenth Edition, 2010, under the functional category of "Esters." Other esters suitable for use in the cosmetic composition include those known as polyhydric alcohol esters and glycerides.

Other suitable oils include amides. Amides include compounds having an amide functional group while being liquid at 25° C. and insoluble in water. Suitable amides include N-acetyl-N-butylaminopropionate, isopropyl N-lauroylsarcosinate, and N,N,-diethyltoluamide. Other suitable amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include $C_{4-20}$ alkyl ethers of polypropylene glycols, and di-$C_{8-30}$ alkyl ethers. Suitable examples of these materials include PPG-14 butyl ether, PPG-15 stearyl ether, dioctyl ether, dodecyl octyl ether, and mixtures thereof.

The cosmetic compositions may include an emulsifier. An emulsifier is particularly suitable when the cosmetic composition is in the form of an emulsion or if immiscible materials are being combined. The cosmetic composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic, zwitterionic, or cationic. Non-limiting examples of emulsifiers are disclosed in U.S. Pat. No. 3,755,560, U.S. Pat. No. 4,421,769, and McCutcheon's, *Emulsifiers and Detergents*, 2010 Annual Ed., published by M. C. Publishing Co. Other suitable emulsifiers are further described in the Personal Care Product Council's *International Cosmetic Ingredient Dictionary and Handbook*, Thirteenth Edition, 2006, under the functional category of "Surfactants—Emulsifying Agents."

Suitable emulsifiers include, but are not limited to, the following classes of ethers and esters: ethers of polyglycols and of fatty alcohols, esters of polyglycols and of fatty acids, ethers of polyglycols and of fatty alcohols which are glycosylated, esters of polyglycols and of fatty acids which are glycosylated, ethers of $C_{12-30}$ alcohols and of glycerol or of polyglycerol, esters of $C_{12-30}$ fatty acids and of glycerol or of polyglycerol, ethers of oxyalkylene-modified $C_{12-30}$ alcohols and of glycerol or polyglycerol, ethers of $C_{12-30}$ fatty alcohols comprising and of sucrose or of glucose, esters of sucrose and of $C_{12-30}$ fatty acids, esters of pentaerythritol and of $C_{12-30}$ fatty acids, esters of sorbitol and/or sorbitan and of $C_{12-30}$ fatty acids, ethers of sorbitol and/or sorbitan and of alkoxylated sorbitan, ethers of polyglycols and of cholesterol, esters of $C_{12-30}$ fatty acids and of alkoxylated ethers of sorbitol and/or sorbitan, and combinations thereof.

Linear or branched type silicone emulsifiers may also be used. Examples of some useful polyether modified silicones include KF-6011, KF-6012, KF-6013, KF-6015, KF-6015, KF-6017, KF-6043, KF-6028, and KF-6038 from Shin Etsu. Examples of some useful silicone emulsifiers include the polyglycerolated linear or branched siloxane emulsifiers including KF-6100, KF-6104, and KF-6105 from Shin Etsu.

Emulsifiers also include emulsifying silicone elastomers. Suitable emulsifying silicone elastomers may include at least one polyalkyl ether or polyglycerolated unit. Polyoxyalylenated emulsifying silicone elastomers that may be used include those sold by Shin-Etsu Silicones under the names KSG-21, KSG-20, KSG-30, KSG-31, KSG-32, KSG-33; KSG-210 (dimethicone/PEG-10/15 crosspolymer dispersed in dimethicone); KSG-310 (PEG-15 lauryl dimethicone crosspolymer); KSG-320 (PEG-15 lauryl dimethicone crosspolymer dispersed in isododecane); KSG-330 (PEG-15 lauryl dimethicone crosspolymer dispersed in triethylhexanoin), KSG-340 (PEG-10 lauryl dimethicone crosspolymer and PEG-15 lauryl dimethicone crosspolymer). Other examples of some silicone emulsifying elastomers are supplied by Dow Corning™, including PEG-12 dimethicone crosspolymers (DC 9010 and 9011). Other examples of some suitable silicone emulsifiers are sold by Dow Corning and include DC9010 and DC9011. Polyglycerolated emulsifying silicone elastomers are disclosed in PCT/WO 2004/024798. Such elastomers include Shin-Etsu's KSG series, such as KSG-710 (dimethicone/polyglycerin-3 crosspolymer dispersed in dimethicone); or lauryl dimethicone/polyglycerin-3 crosspolymer dispersed in a variety of solvent such as isododecane, dimethicone, triethylhexanoin, available as KSG-810, KSG-820, KSG-830, or KSG-840 from Shin-Etsu.

Structuring agents may be used to increase viscosity, thicken, solidify, or provide solid or crystalline structure to the cosmetic composition. Structuring agents are typically grouped based on solubility, dispersibility, and phase compatibility. Examples of aqueous or water structuring agents include, but are not limited to, polymeric agents, natural or synthetic gums, polysaccharides, and the like. The cosmetic compositions may comprise from about 0.0001%, 0.001%, 0.01%, 0.05%, 0.1%, 0.5%, 1%, 2%, 3%, 5% to about 25%, 20%, 10%, 7%, 5%, 4%, or 2%, by weight of the cosmetic composition, of one or more structuring agents.

Polysaccharides and gums may be examples of some suitable aqueous phase thickening agents. Suitable classes of polymeric structuring agents include, but are not limited to, carboxylic acid polymers, polyacrylamide polymers, sulfonated polymers, high molecular weight polyalkylglycols or polyglycerins, copolymers thereof, hydrophobically modified derivatives thereof, and mixtures thereof.

Examples of oil structuring agents include silicone and organic based materials. Suitable ranges of oil structuring agents are from about 0.01%, 0.05%, 0.1% 0.5%, 1%, 2.5%, 5%, or 10% to about 30%, 25%, 20%, 15%, 10%, or 5%. Some examples of suitable oil phase structuring agents include those that are silicone based, such as silicone elastomers, silicone gums, silicone waxes, and linear silicones having a degree of polymerization allowing the silicone to increase the viscosity of the oil phase. Examples of some silicone structuring agents include, but are not limited to, silicone elastomers, silicone gums, and silicone waxes, Suitable silicone elastomers may be in the powder form, or dispersed or solubilized in solvents such as volatile or non-volatile silicones, or silicone compatible vehicles such as paraffinic hydrocarbons or esters. Some examples of silicone elastomer powders include vinyl dimethicone/methicone silsesquioxane crosspolymers like KSP-100, KSP-101, KSP-102, KSP-103, KSP-104, KSP-105, available from Shin-Etsu, hybrid silicone powders that contain a fluoroalkyl group like KSP-200, available from Shin-Etsu, which is a fluoro-silicone elastomer, and hybrid silicone powders that contain a phenyl group such as KSP-300, available from Shin-Etsu, which is a phenyl substituted silicone elastomer; and DC 9506 available from Dow Corning.

Examples of some silicone elastomer dispersions include dimethicone/vinyl dimethicone crosspolymers supplied by a variety of suppliers including Dow Corning Corporation under the tradenames DC9040 or DC9041, Momentive under the tradename SFE 839, or Shin-Etsu Silicones under the tradenames KSG-15, 16, 18. KSG-15 has the INCI name cyclopentasiloxane (and) dimethicone/vinyl dimethicone crosspolymer. KSG-18 has the INCI name diphenylsiloxy phenyl trimethicone (and) dimethicone/phenyl vinyl dimethicone crossoplymer. Silicone elastomers may also be purchased from Grant Industries under the Gransil trademark. Other suitable silicone elastomers have long chain alkyl substitutions such as lauryl dimethicone/vinyl dimethicone crosspolymers supplied by Shin Etsu under the tradenames KSG-41, KSG-42, KSG-43, and KSG-44, wherein the elastomer is dispersed in solvents including mineral oil, isodocane, triethylhexanoin, or squalene, respectively. Other suitable silicone elastomers may have polyglycerine substitutions such as lauryl dimethicone/polyglycerin-3 crosspolymers supplied by Shin Etsu under the tradenames KSG-810, KSG-820, KSG-830, and KSG-840, wherein the elastomer is dispersed in solvents including mineral oil, isodocane, triethylhexanoin, or squalene, respectively. Other suitable silicone elastomers may have polyglycol substitutions such as PEG-15/lauryl dimethicone crosspolymers supplied by Shin Etsu under the tradenames KSG-310, KSG-320, KSG-330, and KSG-340, wherein the elastomer is dispersed in solvents including mineral oil, isodocane, triethylhexanoin, or squalene, respectively. Other suitable silicone elastomers having polyglycol substitutions include Shin Etsu's KSG-210, a dimethicone/PEG-10/15 crosspolymer in dimethicone.

Silicone gums may be used as a structuring agent. The silicone gum may have a viscosity ranging from about 500,000 to 100 million cst at 25° C., from about 600,000 to 20 million, from about 600,000 to 12 million cst. Some suitable silicone gums include those sold by Wacker-Belsil under the trade names CM3092, Wacker-Belsil 1000, or Wacker-Belsil DM 3096. A particularly suitable silicone gum is dimethiconol, available from Dow Corning Corporation under the trade name 1-1254 Fluid, 2-9023 Fluid, and 2-9026 Fluid. Dimethiconol is often sold as a mixture with a volatile or nonvolatile silicone such as Dow Corning 1401 Fluid, 1403 Fluid, and 1501 Fluid.

Another non-limiting example of a structuring agent is silicone wax. Silicone waxes may be referred to as alkyl silicone waxes and may be semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from Evonik Goldschmidt GmbH under the tradename Abil Wax 9800 or from Dow Corning under the tradename 2503. Another example is bis-stearyl dimethicone (which may be purchased from Gransil Industries under the tradename Gransil A-18), behenyl dimethicone, or behenoxy dimethicone.

Other suitable structuring agents include polyamides and polysilicone-polyamide copolymers. Suitable polysilicone-polyamide copolymers are disclosed in U.S. Patent Application Publication No. 2004/0170586.

Other structuring agents may be one or more natural or synthetic waxes such as animal, vegetable, or mineral waxes. Suitable silicone waxes are disclosed in U.S. Pat. Nos. 5,413,781 and 5,725,845, and further include alkylmethyl polysiloxanes, C10-C60 alkyl dimethicones, and mixtures thereof.

Other structuring agents include natural or synthetic montmorillonite minerals, silicas, silicates, silica silylate, and alkali metal or alkaline earth metal derivatives thereof.

The cosmetic compositions may optionally contain one or more UV actives. As used herein, "UV active" includes both sunscreen agents and physical sunblocks. Suitable UV actives may be organic or inorganic. Examples of some suitable UV actives are listed in the functional category of "Sunscreen Agents" in the Personal Care Product Council's *International Cosmetic Ingredient Dictionary and Handbook*, Thirteenth Edition, 2010. Suitable UV actives include those defined or proposed by regulatory agencies in the US (e.g., 21 CFR part 352, 68 Federal Register 41386, 70 Federal Register 72449, or 71 Federal Register 42405), Europe (Regulation No 1223/2009 of the EU Parliament; Annex VI), Japan, China, Australia, New Zealand, or Canada. In some examples, the cosmetic composition may comprise from about 0.01% to about 20%, by weight of the cosmetic composition, of a UV active. The cosmetic composition may also comprise a sufficient amount of one or more UV actives to yield a Sun Protection Factor of at least about 15, 30, 45, or 50. SPF testing is conventional and well understood in the art. A suitable SPF test is prescribed in 21 C.F.R. 352, Subpart D.

Some suitable UV actives include dibenzoylmethane derivatives including 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxy dibenzoylmethane, 4-tert-butyl-4'-methoxy dibenzoylmethane (i.e., butyl methoxydibenzoylmethane or avobenzone) (commercially available as PARSOL® 1789 from DSM), 2-methyl-5-isopropyl-4'-methoxy dibenzoylmethane, 2-methyl-5-tert-butyl-4'-methoxydibenzoylmethane, 2,4-dimethyl-4'-methoxy dibenzoylmethane, and 2,6-dimethyl-4-tert-butyl-4'-methoxy dibenzoylmethane. Some other suitable UV actives include 2-ethylhexyl-p-methoxycinnamate (commercially available as PARSOL® MCX from DSM), 2-hydroxy-4-methoxybenzophenone, benzonphenone-3 (i.e. oxybeznone), octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, titanium dioxide, and mixtures thereof.

Particularly suitable UV actives are 2-ethylhexyl-p-methoxycinnamate, 4-tert-butyl-4'-methoxy dibenzoylmethane, 2-hydroxy-4-methoxybenzo-phenone, 2-phenylbenzimidazole-5-sulfonic acid, octocrylene, zinc oxide, titanium dioxide, and mixtures thereof.

Some other suitable UV actives include 4-methylbenzylidene camphor (commercially available as PARSOL® 5000 from DSM or Eusolex 6300 from Merck), methylene bis-benzotriazolyl tetramethylbutylphenol (i.e., bisoctrizole, commercially available as Tinosorb® M from BASF), bis-ethylhexyloxyphenol methoxyphenol triazine (i.e., bemotrizinol, commercially available as Tinosorb® S from BASF), disodium phenyl dibenzimidazole tetrasulfonate (i.e., Bisdisulizole disodium, commercially available as Neo Heliopan® AP from Symrise), Ethylhexyl triazone (commercially available as Uvinul® T 150 from BASF), Drometrizole trisiloxane (marketed as Mexoryl XL by L'Oreal), Sodium Dihydroxy Dimethoxy Disulfobenzophenone (i.e., benzophenone-9, commercially available as Uvinul® DS 49 from BASF), Diethylamino Hydroxybenzoyl Hexyl Benzoate (commercially available as Uvinul® A Plus from BASF), diethylhexyl butamido triazone (i.e., Iscotrizinol, commercially available as Uvasorb® HEB by 3V Sigma), Polysilicone-15 (i.e., commercially available as PARSOL® SLX from DSM), and Isoamyl p-Methoxycinnamate (i.e., amiloxate, commercially available as Neo Heliopan® E 1000 from Symrise).

The cosmetic compositions may be generally prepared by conventional methods such as those known in the art of making cosmetic compositions. Such methods typically involve mixing of ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The cosmetic compositions are preferably prepared such as to optimize stability (physical stability, chemical stability, photostability, etc.) and/or delivery of active materials. The cosmetic composition may be provided in a package sized to store a sufficient amount of the cosmetic composition for a treatment period. The size, shape, and design of the package may vary widely. Certain package examples are described in U.S. Pat. Nos. D570,707; D391,162; D516,436; D535,191; D542,660; D547,193; D547,661; D558,591; D563,221; 2009/0017080; 2007/0205226; and 2007/0040306.

Melanin Synthesis Assay

A B16-F1 mouse melanoma cell line may be employed as an assay to measure melanin synthesis. The B16-F1 cells may be obtained from American Tissue Culture Collection, Virginia, USA. The cell culture medium that may be used in the assay may comprise 500 mL of Dulbecco's Modified Eagle's Medium (DMEM), 50 mL Fetal Bovine Serum (FBS), and 5 mL of penicillin-streptomycin liquid. B16-F1 cells that are cultured in this medium and grown to greater than 90% confluency synthesize melanin. While not intending to be bound by any theory, it is hypothesized that melanin synthesis is stimulated by the culture medium and/or stress induced by growth to a high confluency. The DMEM and FBS can be obtained from American Tissue Culture Collection and the penicillin-streptomycin liquid can be obtained from Invitrogen, Inc., California, USA. Equipment used in the assay include a $CO_2$ incubator, such as a Forma Series Model 3110 by Therma Scientific, Massachusetts, USA; a hemocytometer, such as a Bright Line model by Hauser Scientific, Pennsylvania, USA; and a UV-Visible Spectrum Plate Reader, such as a SpectraMax250 from Molecular Devices, California, USA. The assay steps may include:

Day 0—Cell Growth: Warm the cell culture medium to 37° C. and place 29 mL into a T-150 flask. Add approximately $1 \times 10^6$ of B16-F1 passage 1 mouse cells to the T-150 flask and incubate for 3 days at 37° C., 5% $CO_2$, 90% relative humidity, until ~80% confluency;

Day 3—Initiate a 96 Well Plate: At day 3, trypsinize the cells from the T-150 flask and determine the concentration of cells using a hemocytometer. Initiate a 96 well plate with 2,500 cells per well in 100 microliters of cell culture medium. Incubate the plate at 37° C., 5% $CO_2$, 90% relative humidity for about 2 days until at least 20% to 40% confluency;

Day 5—Decant the cell culture medium from the plate and replace with fresh culture medium (100 uL per well).

Add 1 microliter of [test compound] diluted in a [water or DSMO] solvent. Multiple dilution ratios may be tested in order to generate a dose response curve, wherein preferably three wells are treated with each dilution ratio. Controls comprise wells having the cell culture medium, B16-F1 cells, and the solvent (control #1); wells comprising the cell culture medium and the solvent (control #2); and optionally wells comprising the cell culture medium, solvent and [test compound] when necessary to control for the [test compound] background color (control #3);

Day 7—Measure Melanin Production: Cells should have a confluency greater than ~90%. If not, this data point is not used. Add 100 microliters of a 0.75% sodium hydroxide solution to each well. Read the 96 well plate using the UV-Vis Plate Reader at 410 nm to optically measure the amount of melanin produced between wells that are treated with [test compound] and control wells that are not treated with a test compound. Wells in which melanin is produced typically appear brownish in color. Wells in which little melanin is produced typically appear clear to light purple in color. Percentage of melanin synthesis inhibition is calculated by the following equation:

$$100 - \frac{[OD410 \text{ Test Compound} - OD410 \text{ Control \#2}]}{(OD410 \text{ Control \#1} - OD410 \text{ Control \#2})} \times 100$$

Where OD410 is the Optical Density at 410 nm as measured by the UV-Vis Spectrum Plate Reader.

When Control #3 is used, the formula for percentage melanin synthesis inhibition is:

$$100 - \frac{[OD410 \text{ Test Compound} - OD410 \text{ Control \#3}]}{(OD410 \text{ Control \#1} - OD410 \text{ Control \#2})} \times 100$$

Using generally the assay outlined above, melanin synthesis in treated B16-F1 cells was inhibited as compared to control cells as shown in Table 1.

Methods of Use

The cosmetic compositions disclosed herein may be applied to one or more skin surfaces and/or one or more mammalian keratinous tissue surfaces as part of a user's daily routine or regimen. Additionally or alternatively, the cosmetic compositions herein may be used on an "as needed" basis. In some examples, an effective amount of the cosmetic composition may be applied to the target portion of the keratinous tissue or skin. In some examples, the cosmetic composition may be provided in a package with written instructions detailing the application regimen.

The method may include a step of identifying a target portion of keratinous tissue or skin comprising one or more of the following for treatment with the cosmetic composition: age spots, pigment spots, uneven skin tone, and/or in need of melanin reduction. The method may also include a step of identifying a skin surface for treatment with the cosmetic composition for improving skin condition. The skin surface may be identified by the user or a third party such as a dermatologist, cosmetician, or other individual or even by a combination of different individuals. Identification may be done, for example, by visual inspection of the skin surface in need of treatment based on size and/or color. Identification may also be done by either custom-made or commercially available imaging devices such as SIAscope V (available from Astron Clinica, Ltd., UK) or the VISTA® Complexion Analysis system (available from Canfield Scientific, Inc., Fairfield, N.J.). Both devices are capable of collecting images of the skin and identifying age spots. Identification may also be done, for example, by color meter or spectrophotometer, which are both capable of collecting skin color information of basal area and/or age spots.

Skin surfaces may include those not typically covered by clothing such as facial skin surfaces, hand and arm skin surfaces, foot and leg skin surfaces, and neck and chest skin surfaces (e.g., décolletage). For example, areas identified for treatment may include areas such as the forehead, perioral, chin, periorbital, nose, and/or cheek skin surfaces. In another example, the cosmetic composition may be applied to any facial skin care surface and/or any other skin surface identified as in need of treatment by the cosmetic composition. In some examples, one or more of these skin surfaces may be identified as needing treatment and one or more of these skins surfaces may be treated with the cosmetic composition.

The method may comprise a step of applying the composition to the skin surface, which may or may not have been previously identified. Many regimens exist for the application of the cosmetic composition. The cosmetic composition may be applied as needed and/or at least once a day, twice a day, or on a more frequent daily basis, during a treatment period. Non-limiting examples of the treatment periods may be between about 1 week and about 12 weeks, between about 4 weeks and about 12 weeks, and/or between about 4 weeks and about 8 weeks. In another example, the treatment period may extend over multiple months (i.e., 3-12 months) or multiple years. In another example, the cosmetic composition may be applied least once a day during a treatment period of at least about 4 weeks or at least about 8 weeks. In another example, the cosmetic composition may be applied twice a day during a treatment period of at least about 4 weeks or 8 weeks. In another example, the cosmetic composition can also be applied to at least one skin surface area at least once per day, twice per day, or three times per day for a period of 7, 14, 21, or 28 days or more. When applied twice daily, the first and second applications may be separated by at least 1 to about 12 hours. The cosmetic composition may be also applied in the morning and/or in the evening before bed. The treatment period should be a sufficient time to provide an improvement in the skin surface but need not be so. Non-limiting examples of improvements include a detectable reductions in the size of the age spot(s), lightening of the age spot(s) (e.g., lighter in color), a decrease in melanin levels, and an improvement in melanin evenness. For general application to keratinous tissue and, particularly a facial skin surface, the dosed amount of the cosmetic composition may be between about 1 to about 50 microliters/cm$^2$ per application (i.e., per single application to the skin surfaces).

EXAMPLES

The following examples are given solely for the purpose of illustration and are not to be construed as limiting the invention, as many variations thereof are possible.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

Examples of some cosmetic compositions are provided below.

TABLE 3

| Component | Ex. A | Ex. B | Ex. C | Ex. D | Ex. E |
|---|---|---|---|---|---|
| Water | QS | QS | QS | QS | QS |
| Glycerin | 10 | 10 | 10 | 10 | 10 |
| Disodium EDTA | 0.1 | 0.1 | 0.1 | 0.1 | 0.1 |
| Undecylenoyl-L-Phenylalanine | 2 | 0.2 | 1 | 1 | 1 |
| Triethanolamine | 0.7 | 0.07 | 0.35 | 0.35 | 0.35 |
| Bisabolol | 2 | 0.1 | 0.1 | 0.1 | 0.1 |
| Tocopheryl Acetate | 0.5 | 0.5 | 0.5 | 0.5 | 0.5 |
| Isohexadecane | 3 | 3 | 3 | 3 | 3 |
| Isopropyl Isostearate | 1.33 | 1.33 | 1.33 | 1.33 | 1.33 |
| Sucrose Polycottonseedate | 0.67 | 0.67 | 0.67 | 0.67 | 0.67 |
| Hexyldecanol | 5 | 0.05 | 5 | 0.05 | 5 |
| Polymethylsilsesquioxane | 0.25 | 0.25 | 0.25 | 0.25 | 0.25 |
| Cetearyl Glucoside, Cetearyl Alcohol | 0.5 | 0.5 | 0.5 | 0.5 | 0.5 |
| Behenyl Alcohol | 0.6 | 0.6 | 0.6 | 0.6 | 0.6 |
| Ethylparaben | 0.2 | 0.2 | 0.2 | 0.2 | 0.2 |
| Propylparaben | 0.1 | 0.1 | 0.1 | 0.1 | 0.1 |
| Cetyl Alcohol | 0.5 | 0.5 | 0.5 | 0.5 | 0.5 |
| Stearyl Alcohol | 0.7 | 0.7 | 0.7 | 0.7 | 0.7 |
| PEG-100 Stearate | 0.2 | 0.2 | 0.2 | 0.2 | 0.2 |
| Polyacrylamide (and) C13-14 Isoparaffine (and) Laureth-7 | 2.25 | 2.5 | 2.25 | 2.25 | 2.5 |
| Panthenol | 1 | 1 | 1 | 1 | 1 |
| Niacinamide | 5 | 5 | 5 | 5 | 0 |
| Benzyl Alcohol | 0.25 | 0.25 | 0.25 | 0.25 | 0.25 |
| Dimethicone and Dimethiconol | 2 | 2 | 2 | 2 | 2 |
| Batyl Alcohol | 2 | 0.5 | 1 | 0.5 | 0.5 |

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any related patent or application identified in the Application Data Sheet accompanying this application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cosmetic composition comprising:
   a. N-undecylenoyl-L-phenylalanine;
   b. hexyldecanol;
   c. bisabolol; and
   d. batyl alcohol.

2. The cosmetic composition of claim 1, wherein the composition further comprises a vitamin B compound.

3. The cosmetic composition of claim 2, wherein the vitamin B compound comprises niacinamide.

4. The cosmetic composition of claim 3, wherein the niacinamide has a concentration of less than about 11%, by weight of the cosmetic composition.

5. The cosmetic composition of claim 1, wherein the hexyldecanol has a concentration of from about 0.01% to about 8%, by weight of the cosmetic composition.

6. The cosmetic composition of claim 1, wherein the hexyldecanol has a concentration of from about 0.05% to about 5%, by weight of the cosmetic composition.

7. The cosmetic composition of claim 1, wherein the batyl alcohol has a concentration of from about 0.03% to about 5%, by weight of the cosmetic composition.

8. The cosmetic composition of claim 1, wherein the batyl alcohol has a concentration of from about 0.03% to about 2%, by weight of the cosmetic composition.

9. The cosmetic composition of claim 1, wherein the bisabolol has a concentration of from about 0.003% to about 2%, by weight of the cosmetic composition.

10. The cosmetic composition of claim 1, wherein the N-undecylenoyl-L-phenylalanine has a concentration of from 0.01% to about 2%, by weight of the cosmetic composition.

11. The cosmetic composition of claim 1, wherein the cosmetic composition further comprises a UV active.

12. The cosmetic composition of claim 1, wherein the cosmetic composition further comprises glycerin.

13. The cosmetic composition of claim 1, wherein the cosmetic composition further comprises a material selected from the group consisting of hydroxycinnamic acid, inositol, licorice extract, glycyrrhetinic acid, glabridin, vitamin E succinate, salicylic acid, *Laminaria Saccharina* extract, *Ficus Bengalensis* extract, N-acetyl glucosamine, and combinations thereof.

14. The cosmetic composition of claim 1, wherein the cosmetic composition is provided in the form of a water-in-oil emulsion, an oil-in-water emulsion, or a water-in-silicone emulsion.

15. A method of reducing melanin synthesis, the method comprising:
   a. identifying a target portion of keratinous tissue in need of melanin reduction; and
   b. topically applying to the target portion of the keratinous tissue an effective amount of a cosmetic composition comprising:
      i. N-undecylenoyl-L-phenylalanine;
      ii. hexyldecanol;
      iii. bisabolol; and
      iv. batyl alcohol.

16. The method of claim 15, wherein the composition further comprises niacinamide.

17. The method of claim 15, wherein the hexyldecanol has a concentration of from about 0.05% to about 5%, by weight of the cosmetic composition.

18. The method of claim 15, wherein the batyl alcohol has a concentration of from about 0.03% to about 5%, by weight of the cosmetic composition.

19. The method of claim 15, wherein the bisabolol has a concentration of from about 0.003% to about 2%, by weight of the cosmetic composition.

20. The method of claim 15, wherein the N-undecylenoyl-L-phenylalanine has a concentration of from 0.01% to about 2%, by weight of the cosmetic composition.

* * * * *